(12) United States Patent
Campton et al.

(10) Patent No.: US 10,871,485 B2
(45) Date of Patent: Dec. 22, 2020

(54) KITS FOR LABELING OF BIOMARKERS AND METHODS OF USING THE SAME

(71) Applicant: RareCyte, Inc., Seattle, WA (US)

(72) Inventors: Daniel E. Campton, Seattle, WA (US); Yao Sun, Seattle, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

(21) Appl. No.: 16/383,227

(22) Filed: Apr. 12, 2019

(65) Prior Publication Data

US 2019/0317080 A1 Oct. 17, 2019

Related U.S. Application Data

(60) Provisional application No. 62/657,517, filed on Apr. 13, 2018.

(51) Int. Cl.
| | | |
|---|---|---|
| *G01N 33/52* | (2006.01) | |
| *G01N 33/58* | (2006.01) | |
| *G01N 33/53* | (2006.01) | |
| *G01N 33/68* | (2006.01) | |

(52) U.S. Cl.
CPC ....... *G01N 33/526* (2013.01); *G01N 33/5308* (2013.01); *G01N 33/582* (2013.01); *G01N 33/6803* (2013.01); *G01N 2800/60* (2013.01); *G01N 2800/70* (2013.01)

(58) Field of Classification Search
None
See application file for complete search history.

(56) References Cited

U.S. PATENT DOCUMENTS

| | | |
|---|---|---|
| 5,002,867 A | 3/1991 | Macevicz |
| 5,391,723 A | 2/1995 | Priest |
| 5,453,355 A | 9/1995 | Birkenmeyer et al. |
| 5,599,668 A | 2/1997 | Stimpson et al. |
| 5,650,334 A | 7/1997 | Zuk et al. |
| 5,830,645 A | 11/1998 | Pinkel et al. |
| 5,849,878 A | 12/1998 | Cantor et al. |
| 5,952,202 A | 9/1999 | Aoyagi et al. |
| 6,046,038 A | 4/2000 | Nilsen |
| 6,110,687 A | 8/2000 | Nilsen |
| 6,117,631 A | 9/2000 | Nilsen |

(Continued)

FOREIGN PATENT DOCUMENTS

| | | |
|---|---|---|
| WO | WO 93/01498 | 1/1993 |
| WO | WO 2015/086549 A1 | 6/2015 |
| WO | WO 2018/017604 A1 | 1/2018 |

OTHER PUBLICATIONS

Schriml et al., "Tyrannide Signal Amplification (TSA)-FISH Applied to Mapping PCR-Labeled Probes Less than 1kb in Size," BioTechniques, September, vol. 27, No. 3, pp. 608-613. (Year: 1999).*

(Continued)

*Primary Examiner* — Young J Kim
(74) *Attorney, Agent, or Firm* — Shay Glenn LLP

(57) ABSTRACT

Kits, compositions, and methods for labeling target materials or target analytes are considered. The composition can include one or more affinity molecules indirectly conjugated to one or more detection moieties. The kit can be used to detect a single biomarker or multiple biomarkers. The kit can be used to perform a single round of labeling or multiple rounds of labeling.

22 Claims, 4 Drawing Sheets

(56) References Cited

U.S. PATENT DOCUMENTS

| | | |
|---|---|---|
| 6,203,989 B1 | 3/2001 | Goldberg et al. |
| 6,207,385 B1 | 3/2001 | Stanley |
| 6,245,513 B1 | 6/2001 | Lane et al. |
| 6,344,329 B1 | 2/2002 | Lizardi |
| 6,451,588 B1 | 9/2002 | Egholm et al. |
| 6,531,283 B1 | 3/2003 | Kingsmore et al. |
| 6,558,928 B1 | 5/2003 | Landegren |
| 6,617,138 B1 | 9/2003 | Rudi et al. |
| 6,803,196 B1 | 10/2004 | Lyon et al. |
| 6,890,741 B2 | 5/2005 | Fan et al. |
| 6,921,642 B2 | 7/2005 | Kingsmore et al. |
| 7,074,564 B2 | 7/2006 | Landegren |
| 7,186,814 B2 | 3/2007 | Garimella et al. |
| 7,192,703 B2 | 3/2007 | Sun et al. |
| 7,419,786 B2 | 9/2008 | Kurane et al. |
| 7,767,394 B2 | 8/2010 | Turner et al. |
| 7,776,617 B2 | 8/2010 | Lee et al. |
| 7,901,949 B2 | 3/2011 | Raj |
| 7,910,294 B2 | 3/2011 | Karlsen |
| 7,972,837 B2 | 7/2011 | Lee et al. |
| 8,309,306 B2 | 11/2012 | Nolan et al. |
| 8,574,833 B2 | 11/2013 | Jenison et al. |
| 8,658,388 B2 | 2/2014 | Harvey et al. |
| 8,946,389 B2 | 2/2015 | Gao et al. |
| 9,212,394 B2 | 12/2015 | Fehr et al. |
| 9,222,936 B2 | 12/2015 | Schwartz et al. |
| 9,250,243 B2 | 2/2016 | Singh et al. |
| 9,376,717 B2 | 6/2016 | Gao et al. |
| 9,567,639 B2 | 2/2017 | Oliphant et al. |
| 9,663,818 B2 | 5/2017 | Flor et al. |
| 9,695,394 B1 | 7/2017 | Coelho et al. |
| 9,714,937 B2 | 7/2017 | Dunaway |
| 9,821,111 B2 | 11/2017 | Coelho et al. |
| 9,909,167 B2 | 3/2018 | Samusik et al. |
| 9,944,972 B2 | 4/2018 | Yin et al. |
| 2003/0170613 A1 | 6/2003 | Strauss |
| 2004/0014078 A1 | 1/2004 | Xia et al. |
| 2004/0018577 A1 | 1/2004 | Emerson Campbell et al. |
| 2004/0091857 A1 | 5/2004 | Nallur et al. |
| 2004/0137493 A1 | 7/2004 | Goldberg et al. |
| 2005/0069939 A1 | 3/2005 | Wang et al. |
| 2005/0095627 A1 | 5/2005 | Kolman et al. |
| 2005/0208589 A1 | 9/2005 | Stupp et al. |
| 2006/0014172 A1 | 1/2006 | Muller et al. |
| 2006/0194222 A1 | 8/2006 | Sorge et al. |
| 2007/0161043 A1 | 7/2007 | Nie et al. |
| 2008/0206853 A1 | 8/2008 | Lee et al. |
| 2009/0041717 A1 | 2/2009 | MacDonald et al. |
| 2009/0053169 A1 | 2/2009 | Castillo et al. |
| 2010/0015607 A1 | 1/2010 | Geiss et al. |
| 2010/0167945 A1 | 7/2010 | Singh et al. |
| 2010/0248231 A1 | 9/2010 | Wei et al. |
| 2011/0086774 A1 | 4/2011 | Dunaway |
| 2012/0252685 A1 | 10/2012 | Treynor et al. |
| 2012/0258870 A1 | 10/2012 | Schwartz et al. |
| 2012/0258880 A1 | 10/2012 | Schwartz et al. |
| 2012/0258881 A1 | 10/2012 | Schwartz et al. |
| 2013/0035259 A1 | 2/2013 | Schwartz et al. |
| 2013/0123121 A1 | 5/2013 | Schwartz et al. |
| 2013/0184184 A1 | 7/2013 | Schwartz et al. |
| 2015/0182596 A1 | 7/2015 | Lee et al. |
| 2015/0368697 A1 | 12/2015 | Samusik et al. |
| 2016/0002701 A1 | 1/2016 | Farrell et al. |
| 2016/0319328 A1 | 11/2016 | Yin et al. |
| 2017/0107563 A1 | 4/2017 | Samusik et al. |
| 2017/0137864 A1 | 5/2017 | Yin et al. |
| 2017/0254813 A1 | 9/2017 | Bieniarz et al. |
| 2017/0327876 A1 | 11/2017 | Khafizov et al. |
| 2018/0216159 A1 | 8/2018 | Yin et al. |

OTHER PUBLICATIONS

Amann et al. Fluorescent-Oligonucleotide Probing of Whole Cells for Determinative, Phylogenetic, and Environmental Studies in Microbiology. Jrnl of Bacteriology, Feb. 1990.

Algar et al. Adsorption and Hybridization of Oligonucleotides . . . , Langmuir, 2006, 22 (26), pp. 11346-11352.

Van Gijlswijk et al. Fluorochrome-labeled Tyramides: Use in Immunocytochemistry and Fluorescence In Situ Hybridization, J Histochem Cytochem 1997 45: 375.

Hendrickson et al. High sensitivity multianalyte immunoassay using covalent DNA-labeled antibodies and polymerase chain reaction, Nucleic Acids Research, 1995, vol. 23, No. 3.

Schweitzer et al. Immunoassays with rolling circle DNA amplification: A versatile platform for ultrasensitive antigen detection PNAS u Aug. 29, 2000, vol. 97, No. 18.

Sano et al. Immuno-PCR: Very Sensitive Antigen Detection by Means of Specific Antibody-DNA Conjugates, Science, New Series, vol. 258, No. 5079, Genome Issue (Oct. 2, 1992).

Walker et al. Improved Cellular Delivery of Antisense Oligonucleotides . . . , Pharm. Res., vol. 12, No. 10, 1995, p. 1548.

Otsuka et al. PEGylated nanoparticles for biological and pharmaceutical applications, Advanced Drug Delivery Reviews 55 (2003) 403-419.

Hatch et al. Rolling circle amplification of DNA . . . , Genetic Analysis: Biomolecular Engineering 15 (1999) 35-40.

Schweller et al. Multiplexed In Situ Immunofluorescence Using Dynamic DNA Complexes, Angew. Chem. Int. Ed. 2012, 51, 9292-9296.

Winzell, Ann; Surface modification of CdSe(Zns) quantum dots for biomedica applications; Dept. of Physics, Chem. and Bio. Master's thesis; 69 pgs; 2010.

\* cited by examiner

US 10,871,485 B2

KITS FOR LABELING OF BIOMARKERS AND METHODS OF USING THE SAME

CROSS-REFERENCE TO RELATED APPLICATIONS

This application claims the benefit of U.S. Provisional Application No. 62/657,517, filed Apr. 13, 2018, which is hereby incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This disclosure relates generally to detection and, in particular, to labeling biomarkers on target analytes.

BACKGROUND

Samples often include materials or analytes of interest that are to be imaged for analysis. These materials or analytes of interest can include a plurality of biomarkers and/or components for which it can be desirous to detect and image. As a result, practitioners, researchers, and those working with samples seek systems and methods to more efficiently and accurately image target materials or analytes of a sample.

DETAILED DESCRIPTION

Figure 1A:
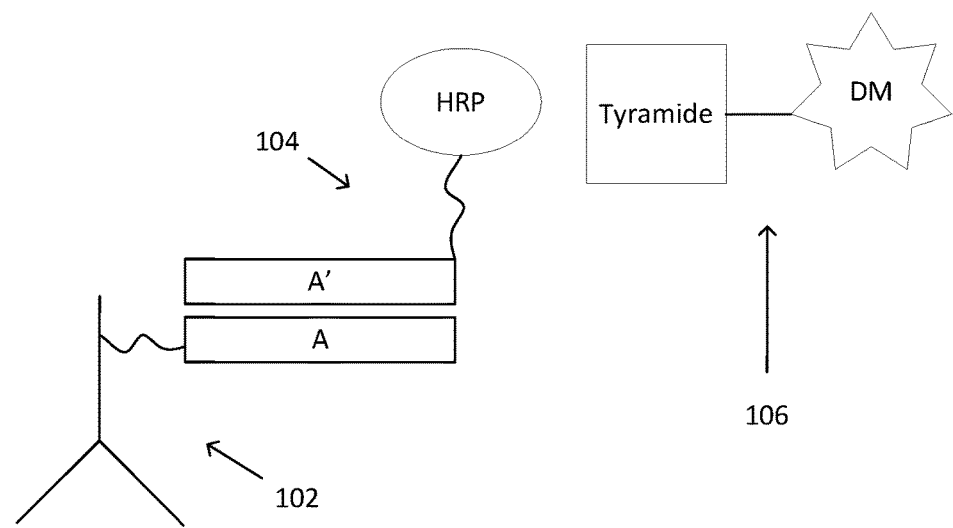
FIGS. 1A, 1B and 1C show example detection kits.

Kits, compositions, and methods for labeling target materials or target analytes are considered. The composition can include one or more affinity molecules indirectly conjugated to one or more detection moieties. The kit can be used to detect a single biomarker or multiple biomarkers. The kit can be used to perform a single round of labeling or multiple rounds of labeling.

In the following descriptions, the term "light" is used to describe various uses and aspects of multiplexing and imaging. The term light is not intended to be limited to describing electromagnetic radiation in the visible portion of the electromagnetic spectrum, but is also intended to describe radiation in the ultraviolet and infrared portions of the electromagnetic spectrum.

In the following descriptions, the term "sample" is used to describe a biological fluid, a biological semi-solid, a biological solid (which can remain solid, such as tissue, or can be liquefied in any appropriate manner), a suspension, a portion of the suspension, a component of the suspension, a cell culture, or the like. For example, for anticoagulated whole blood, the sample is the anticoagulated whole blood (i.e., a suspension), the buffy coat (i.e., a portion of the suspension), or a circulating tumor cell (i.e., a component of the suspension). For the sake of convenience, the sample referenced is whole blood, though it should be understood that the method and system described and discussed herein is used with any appropriate sample, such as urine, blood, bone marrow, buffy coat, cystic fluid, ascites fluid, stool, semen, cerebrospinal fluid, nipple aspirate fluid, saliva, amniotic fluid, mucus membrane secretions, aqueous humor, vitreous humor, vomit, vaginal fluid, and any other physiological fluid, tissue, or semi-solid. For example, the sample can be a tissue sample or a material from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, or a bladder.

In the following descriptions, the terms "target analyte" or "target material" are used to describe a biological material of interest. It should also be understood that the target analyte can be a fraction of a sample, such as buffy coat, a cell, such as ova, fetal material (such as trophoblasts, nucleated red blood cells, fetal red blood cells, fetal white blood cells, fetal DNA, fetal RNA, or the like), a circulating tumor cell ("CTC"), a circulating endothelial cell, an immune cell (e.g., naïve or memory B cells or naïve or memory T cells), a mesenchymal cell, a stem cell, a vesicle, such as an exosome, a liposome, a protein, a nucleic acid, a biological molecule, a naturally occurring or artificially prepared microscopic unit having an enclosed membrane, parasites (e.g., spirochetes, such as Borrelia burgdorferi which cause Lyme disease; malaria-inducing agents), microorganisms, viruses, inflammatory cells, or a portion of a cell culture. For example, the target analyte is a tumor cell from adipose tissue, an adrenal gland, bone marrow, a breast, a caudate, a cerebellum, a cerebral cortex, a cervix, a uterus, a colon, an endometrium, an esophagus, a fallopian tube, a heart muscle, a hippocampus, a hypothalamus, a kidney, a liver, a lung, a lymph node, an ovary, a pancreas, a pituitary gland, a prostate, a salivary gland, a skeletal muscle, skin, a small intestine, a large intestine, a spleen, a stomach, a testicle, a thyroid gland, or a bladder.

In the following descriptions, the term "non-target analyte" is used to describe a biological material which is not a target analyte.

In the following descriptions, the term "biomarker" is used to describe a substance that is present on or within the target analyte or target material (i.e., intracellular or extracellular the target analyte; internalized, such as through phagocytosis, within the target analyte; or the like). Biomarkers include, but are not limited to, peptides, proteins, subunits, domains, motifs, epitopes, isoforms, DNA, RNA, or the like. The biomarker can be a target molecule for drug delivery.

The biomarker or biomarkers include, but are not limited to: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAMS, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CC1, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD31, CD32, CD33 (p67 proteins), CD34, CD38, CD40, CD40L, CD44, CD45, CD46, CD49a, CD52, CD54, CD55, CD56, CD61, CD64, CD66b, CD66e, CD74, CD80 (B7-1), CD89, CD95, CD105, CD123, CD137, CD138, CD140a, CD144, CD146, CD147, CD148, CD152, CD164, CEACAM5, CFTR, cGMP, CINC, *Clostridium botulinum* toxin, *Clostridium peffringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin, DAN, DCC, DcR3, DC-SIGN, Decay accelerating factor, des(1-3)-IGF-I (brain IGF-1), Dhh, digoxin, DLL3, DNAM-1, Dnase, Dpp, DPPIV/CD26, Dtk, EGAD, EDA, EDA-A1, EDA-A2, EDAR, EGF, EGFR (ErbB-1), EMA, EMMPRIN, ENA, endothelin receptor, ER, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), fibronectin, Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-1, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), Ki67, laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, M30, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGD2, PIN, PLA2, placental alkaline phosphatase (PLAP), PIGF, PLP, PP14, Proinsulin, Prorelaxin, Protein C, PR, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFα, TNF-RI, TNF-RII, TNFRSF10A (TRAIL R1 Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITRAITR), TNFRSF19 (TROY TAJ, TRADE), TNFRSF19L (RELT), TNFRSF1A (TNF R1CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1 BB CD137, ILA), TNFRSF21 (DR6), TNFRSF22 (DCTRAIL R2TNFRH2), TNFRST23 (DCTRAIL R1 TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1 B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Vimentin, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors. The biomarkers include proteins, subunits, domains, motifs, isoforms, and/or epitopes belonging to the list above.

In the following descriptions, the term "affinity molecule" is used to describe any molecule that is capable of binding or interacting with a biomarker. The interaction or binding can be covalent or non-covalent. The affinity molecule includes, but is not limited to, an antibody, a hapten, a protein, an aptamer, an oligonucleotide, a polynucleotide, or any appropriate molecule for interacting with or binding to the biomarker.

In the following descriptions, the term "detection moiety" is used to describe a compound or substance which provides a signal for detection, thereby indicating the presence of another compound or substance, an analyte, or the like within a sample or specimen. The detection moiety can be fluorescent, such as a fluorescent probe, or chromogenic, such as a chromogenic dye. The fluorescent probe can be a reactive dye, an organic dye, a fluorescent protein, a quantum dot, non-protein organic molecules, a nanoparticle (e.g., nanodiamond), or the like. The detection moiety can be used as a tracer, as a label for certain structures, as a label for biomarkers, or the like. The detection moiety can be distributed or can label the appropriate structure or biomarkers in manners including, but not limited to, uptake, selective uptake, diffusion, and attachment to a linking molecule. The detection moiety can be bound to the biomarker by direct or indirect conjugation.

The chromogenic dye, which can be used with various enzyme labels (e.g., horseradish peroxidase and alkaline phosphate), includes, but is not limited to, 3,3'-Diaminobenzidine (DAB), 3-Amino-9-Ethylcarbazole (AEC), 4-Chloro-1-Naphtol (CN), P-Phenylenediamine Dihydrochloride/pyrocatechol (Hanker-Yates reagent), Fast Red TR, New Fuchsin, Fast Blue BB, or the like. Fluorescent probes include, but are not limited to 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AutoFluorescent Protein; Alexa Fluor350™; Alexa Fluor430™; Alexa Fluor488™; Alexa Fluor 532™; Alexa Fluor546™; Alexa Fluor568™; Alexa Fluor594™; Alexa Fluor 633™; Alexa Fluor 647™; Alexa Fluor660™; Alexa Fluor680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAGTM FQ; Auramine; Aurophosphine G; Aurophosphine; BAO TAG™ CBQCA; ATTO-TAG™ FQ; Auramine; Aurophosphine G; Aurophosphine; BAO 9(Bisaminophenyloxadiazole); BCECF (high pH); BCECF (low pH); Berberine Sulphate; Beta Lactamase; BFP blue shifted GFP (Y66H; Blue Fluorescent Protein); BFP/GFP FRET; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Brilliant Violet 421; Brilliant Violet 510; Brilliant Violet 605; Brilliant Violet 650; Brilliant Violet 711; Brilliant Violet 786; BTC; BTC-SN; Calcein; Calcein Blue; Calcium Crimson™; Calcium Green; Calcium Green-1; Calcium Green-2; Calcium Green-SN; Calcium Green-C18; Calcium Orange; Calcofluor White; Carboxy-X-hodamine (5-ROX); Cascade Blue™; Cascade Yellow; Catecholamine; CCF2 (GeneBlazer); CFDA; CFP (Cyan Fluorescent Protein); CF405S; CF488A; CF 488; CF 543; CF 647; CF 750; CF 760; CF 780; FP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); CyQuant Cell Proliferation Assay; Dabcyl; Dansyl; Dansyl Amine; Dansyl Cadaverine; Dansyl Chloride; Dansyl DHPE; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS; DiA (4-Di-16-ASP); Dichlorodihydrofluorescein Diacetate (DCFH); DiD-Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP (Enhanced Blue Fluorescent Protein); ECFP (Enhanced Cyan Fluorescent Protein); EGFP (Enhanced Green Fluorescent Protein); ELF 97; Eosin; ER-Tracker™ Green; ER-Tracker™ Red; ER-Tracker™ Blue-White DPX; Erythrosin; Erythrosin ITC; Ethidium Bromide; Ethidium homodimer-1 (EthD-1); Euchrysin; EukoLight; Europium (III) chloride; EYFP (Enhanced Yellow Fluorescent Protein); Fast Blue; FDA; FIF (Formaldehyde Induced Fluorescence); FITC; FITC Antibody; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2, high calcium; Fura-2, low calcium; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; Calcein/Ethidium homodimer; LOLO-1; LO-PRO-1; *Lucifer* Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green; Mitotracker Orange; Mitotracker Red; Mitramycin; Monobromobimane; Monobromobimane (mBBr-GSH); Monochlorobimane; MPS (Methyl Green Pyronine Stilbene); mStrawberry; NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B; Phycoerythrin R; PKH26 (Sigma); PKH67; PMIA; Pontochrome Blue Black; POPO-1; POPO-3; PO-PRO-1; PO-PRO-3; Primuline; Procion Yellow; Propidium Iodid (PI); Pyrene; Pyronine; Pyronine B; Pyrozal Brilliant Flavin 7GF; QD400; QD425; QD450; QD500; QD520; QD525; QD530; QD535; QD540; QD545; QD560; QD565; QD570; QD580; QD585; QD590; QD600; QD605; QD610; QD620; QD625; QD630; QD650; QD655; QD705; QD800; QD1000; QSY 7; Quinacrine Mustard; Red 613 (PE-TexasRed); Resorufin; RFP; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoeryth-rin; rsGFP (red shifted GFP (S65T)); S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgGFP™ (super glow GFP; SITS (Primuline); SITS (Stilbene Isothiosulphonic Acid); SNAFL calcein; SNAFL-1; SNAFL-2; SNARF calcein; SNARFl; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; SYTOX Red; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TetramethylRodamineIsoThioCyanate; True Blue; TruRed; Tubulin Tracker™ Green; Ultralite; Uranine B; Uvitex SFC; wt GFP (wild type GFP); WW 781; X-Rhodamine; XRITC; Xylene Orange; Y66F; Y66H; Y66W; Yellow GFP (Yellow shifted); Green Fluorescent Protein; YFP (Yellow Fluorescent Protein); YO-PRO-1; YO-PRO-3; YOYO-1; YOYO-3; combinations and derivatives thereof; or the like. In one embodiment, the detection moiety, such as organic fluorophore, can have a molecular weight of at least 1 kD, including, without limitation, at least 10 kD, at least 25 kD, at least 50 kD, at least 75 kD, at least 100 kD, at least 150 kD, at least 200 kD, at least 250 kD, at least 300 kD, at least 340 kD, at least 350 kD, at least 500 kD, and at least 750 kD. It should be noted that a nuclear stain, such as Sytox, can be used in combination with a quantum dot.

In the following descriptions, the term "signal disrupter" is used to describe an agent to reduce or eliminate the signal provided by the detection moiety by modifying the detection moiety, removing the detection moiety from the sample, separating the detection moiety from the target analyte, or the like. The signal disrupter can be heat (for example, up to 120° C., including at least 30° C., 40° C., 50° C., 60° C., 70° C., 80° C., 90° C., 95° C., 100° C., 105° C., 110° C., 115° C., or 119° C.), light, chemicals, enzymes, molecules having a higher affinity, buffers, combinations thereof, and the like. The signal disrupter can reduce or eliminate the signal by, for example, elution, denaturation, degradation, cleavage, modification, washing, displacement, photobleaching, heating, quenching, combinations thereof, or any appropriate manner in which to reduce or eliminate the signal. For example, the signal disrupter can be a molecule with a higher affinity (i.e., strand displacement) that separates the detection moiety from the target analyte by strand displacement (the detection moiety can be washed away prior to imaging). As another example, the signal disrupter can be heat which denature oligonucleotides to which the detection moiety is bound, thereby causing the detection moiety to be separated from the target analyte (the detection moiety can be washed away prior to imaging). One or more signal disrupters can be used to reduce or eliminate the signal or signals provided by one or more detection moieties, such as when labeling a single biomarker, when performing multiplexing (i.e., labeling multiple biomarkers in a given round), when performing cyclic labeling (i.e., labeling multiple biomarkes across multiple rounds), or any other appropriate labeling method where it is desirous or advantageous to remove one or more signals.

In the following descriptions, the terms "stain" or "label," which are used interchangeably, are used to describe an affinity molecule bound to or interacted with a detection moiety. In one embodiment, the binding or interaction can be direct. Direct binding or interaction includes covalent or non-covalent interactions between the biomarker and the detection moiety (for example, via an intermediary molecule). In one embodiment, the binding or interaction can be indirect. Indirect binding or interaction includes a binding pair. For example, in one embodiment, the use of at least first and second complementary molecules form binding pairs. The first and second complementary molecules are, in combination, binding pairs which bind or interact in at least one of the following manners: hydrophobic interactions, ionic interactions, hydrogen bonding interactions, non-covalent interactions, covalent interactions, affinity interactions, or the like. The binding pairs include, but are not limited to, immune-type binding-pairs, such as, antigen-antibody, antigen-antibody fragment, hapten-anti-hapten, or primary antibody-secondary antibody; non-immune-type binding-pairs, such as biotin-avidin, biotin-streptavidin, folic acid-folate binding protein, hormone-hormone receptor, lectin-specific carbohydrate, enzyme-enzyme, enzyme-substrate, enzyme-substrate analog, enzyme-pseudo-substrate (substrate analogs that cannot be catalyzed by the enzymatic activity), enzyme-cofactor, enzyme-modulator, enzyme-inhibitor, or vitamin B 12-intrinsic factor. Other suitable examples of binding pairs include complementary nucleic acid fragments (including complementary nucleotides, oligonucleotides, or polynucleotides); Protein A-antibody; Protein G-antibody; nucleic acid-nucleic acid binding protein; polymeric linkers (e.g., polyethylene glycol); or polynucleotide-polynucleotide binding protein. The binding pairs can be included within or used as amplification techniques. Amplification techniques are also implemented to increase the number of detection moieties bound to or interacted with the biomarker to increase a signal. In one embodiment, when binding pairs are used, the stain can be pre-conjugated, such that, during a labeling, staining, or adding step, the affinity molecule is already bound to or interacted with a detection moiety when added to the sample. In one embodiment, when binding pairs are used, the stain can be conjugated in the sample, such that the labeling, staining, or adding step includes at least two sub-steps including introducing (in any desired or appropriate order) an affinity molecule-first binding molecule conjugate and a second binding pair molecule-detection moiety conjugate, wherein the first and second binding pair molecules are complementary and bind to or interact with each other.

Furthermore, "a plurality of stains" can be used to describe two or more stains in which the affinity molecules and/or the detection moieties are different. For example, anti-CK-CF647 is different than anti-EpCAM-CF647. As another example, anti-CK-CF647 is different than anti-CK-CF488.

In the following descriptions, the term "conjugate" is used to describe a first chemical, molecule, moiety, or the like bound to or interacted with a second chemical, molecule, moiety, or the like. The binding or interaction is direct or indirect. Direct binding or interaction includes covalent or non-covalent interactions between the biomarker and the detection moiety (for example, via an intermediary molecule). Indirect binding or interaction includes the use of a binding pair. The first and second complementary molecules, which form a binding pair, bind or interact in at least one of the following manners: hydrophobic interactions, ionic interactions, hydrogen bonding interactions, non-covalent interactions, covalent interactions, affinity interactions, or the like. The binding pairs include, but are not limited to, immune-type binding-pairs, such as, antigen-antibody, antigen-antibody fragment, hapten-anti-hapten, or primary antibody-secondary antibody; nonimmune-type binding-pairs, such as biotin-avidin, biotin-streptavidin, folic acid-folate binding protein, hormone-hormone receptor, lectin-specific carbohydrate, enzyme-enzyme, enzyme-substrate, enzyme-substrate analog, enzyme-pseudo-substrate (substrate analogs that cannot be catalyzed by the enzymatic activity), enzyme-cofactor, enzyme-modulator, enzyme-inhibitor, or vitamin B 12-intrinsic factor. Other suitable examples of binding pairs include complementary nucleic acid fragments (including complementary nucleotides, oligonucleotides, or polynucleotides); Protein A-antibody; Protein G-antibody; nucleic acid-nucleic acid binding protein; polymeric linkers (e.g., polyethylene glycol); or polynucleotide-polynucleotide binding protein.

In the following descriptions, the term "binding pair" is used to describe two molecules which are complementary to each other and capable of binding to or interacting with each other.

In the following descriptions, the term "complementary molecule" is used to describe one molecule of a binding pair.

In the following descriptions, the terms "intermediary molecule," "linker," or "adaptor molecule," which are interchangeable, are used to describe a moiety that connects two parts of a conjugate. For example, an intermediary molecule can be protein A, protein G, antibody, portion of an antibody, antigen, receptor ligand, receptor, ligand binding fragment of a receptor, an aptamer, a polymer, or the like. For example, the intermediary molecule can be succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond (from S-HyNic/S-4FB reaction), zero-length peptide bond (between —COOH and —NH2 directly on affinity molecule and nucleic acid), two peptide bonds on a spacer (from cross-linking of two —NH2 groups), triazole bond (from "click" reaction), a phosphodiester linkage, a phosphorothioate linkage, a polyethylene glycol linkage, a bi-functional crosslinker comprising maleimide and N-hydroxysuccinimide (or similar amine reactive chemicals—for example, tetrafluorophenyl ester ("TFP")), any combination thereof, or the like. For example, the intermediary molecule can be a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylhetecroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

An example method for labeling a biomarker on a target analyte is discussed. In one embodiment, a sample, such as blood, is obtained, such as by venipuncture. The sample is suspected of including at least one target analyte. Suitable devices, systems, and/or methods of sample collection and/or processing can include those described in one or more of the following U.S. patents and published applications, each of which is hereby incorporated by reference in its entirety: U.S. Pat. Nos. 7,074,577; 7,220,593; 7,329,534; 7,358,095; 7,629,176; 7,915,029; 7,919,049; 8,012,742; 9,039,999; 9,217,697; 9,492,819; 9,513,291; 9,533,303; 9,539,570; 9,541,481; 9,625,360; 2014/0161688; 2017/0014819; 2017/0059552; 2017/0074759. Suitable devices, systems, and/or methods for target analyte retrieval, isolation, or picking can include those described in one or more of the following U.S. patents and published applications, each of which is hereby incorporated by reference in its entirety: U.S. Pat. Nos. 9,222,953; 9,227,188; 9,440,234; 9,519,002; 9,810,605; 2017/0219463; 2017/0276575.

The sample is then dispensed onto or into at least one analysis platform. The analysis platform is a microscope slide, a positively charged microscope slide, a negatively charged microscope slide, a coated microscope slide, a porous slide, a micro-well slide, a well plate, a coverslip, a cell microarray, or the like. The analysis platform can be any appropriate material, including, but not limited to, glass, plastic, ceramic, metal, or the like.

In one embodiment, the sample is re-suspended in an attachment solution in a vessel prior to being dispensed onto the analysis platform. For example, the attachment solution is added to or mixed with the sample. The re-suspended sample, which includes at least a portion of the attachment solution is dispensed onto or into the analysis platform by a dispenser, such as a pipet or repeating pipet.

In one embodiment, the sample is spread across the analysis platform. In one embodiment, the sample is spread across the analysis platform by a spreader, such as a squeegee, a pipet tip, a blade, a two-piece spreader including a blade and a base. In one embodiment, the sample is spread across the analysis platform by centrifuging, wetting, or nutating the analysis platform.

In one embodiment, the re-suspended sample is cured to adhere the re-suspended sample to the analysis platform. In one embodiment, the re-suspended sample is dispensed onto the analysis platform and cured without being spread across the analysis platform. Curing occurs in air, such as at room temperature; in an environmentally-controlled chamber, such as at 37° C.; or the like. Furthermore, the sample can undergo an additional fixation step, such as in treatment with formalin or any appropriate fixative, after the curing step has been completed.

In one embodiment, at any point prior to staining, autofluorescence can be reduced or eliminated, such as by bleaching the sample with a chemical (for example, hydrogen peroxide), an enzyme, light, heat, or the like.

The sample then undergoes staining. At least one stain is added to the sample for labeling, such as by an autostainer or manually by an operator. In one embodiment, the at least one target analyte is stained. In one embodiment, at least one non-target analyte or non-target material is stained. In one embodiment, the at least one target analyte and the at least one non-target analyte or materials are stained.

In one embodiment, the sample can undergo staining after collection of the sample. In one embodiment, the sample can undergo staining after processing the sample. In one embodiment, one or more stains (i.e., multiplexing) can be added to the sample. At least one stain is added to the sample for labeling, such as by an autostainer or manually by an operator. In one embodiment, the at least one target analyte is stained. In one embodiment, at least one non-target analyte or non-target material is stained. In one embodiment, the at least one target analyte and the at least one non-target analyte or materials are stained.

After staining, the sample can be imaged, whereby the stained sample is illuminated with one or more wavelengths of excitation light, such as infrared, red, blue, green, and/or ultraviolet, from a light source, such as a laser or a light-emitting diode. The imaging can be done with a flow cytometer or a microscope, such as a fluorescent microscope, a scanner, or any other appropriate imaging system or modality. In one embodiment, imaging can be performed in a system in which a detection moiety, when imaged, can provide a signal across a spectrum, including, without limitation, brightfield and/or darkfield illumination, fluorescence, and the like. The images formed can be overlaid when a plurality of detection moieties are used. Emission, reflection, diffraction, scatter, and combinations thereof are used for detection/imaging. The images can be analyzed to detect, enumerate, and/or locate the target analyte, such as when it is desirous to retrieve or pick the target analyte. Imaging is performed in a tube, on a microscope slide, or in any appropriate vessel or substrate for imaging.

The methods can be performed by at least one of an imaging microscope, a scanner, a flow cytometer, or a microfluidic device, such as a chip or a microchannel, or the method can be performed by any combination of the above. The methods described can be used in a system in which a detection moiety, when imaged, can provide a signal across a spectrum, including, without limitation, at least one of brightfield and/or darkfield illumination, phase contrast, differential interference contrast, fluorescence, and Hoffman modulation contrast imaging or detection.

Though "a biomarker" is discussed, any number of biomarkers of a target analyte or a target material can be labeled for multiplexing purposes. In one embodiment, a first affinity molecule can be selected to bind or interact with a first biomarker on the target analyte. For example, an EpCAM antibody can be selected as the first affinity molecule to bind or interact with an EpCAM biomarker on the target analyte. In another embodiment, such as for multiplexing, a plurality of affinity molecules (i.e., at least a first affinity molecule and a second affinity molecule) can be selected to bind to or interact with a plurality of biomarkers on the target analyte, where each of the plurality of affinity molecules is directed to a different biomarker on the target analyte. The first and second affinity molecules can be bound to the same type of detection moiety or different types of detection moieties. For example, an EpCAM antibody can be selected as the first affinity molecule to bind or interact with an EpCAM biomarker on the target analyte, and a HER2 antibody can be selected as the second affinity molecule to bind or interact with a HER2 biomarker on the target analyte. Furthermore, when a plurality of affinity molecules and detection moieties (i.e., first, second, etc. affinity molecules; and first, second, etc. detection moieties) are used, the respective complementary molecules are selected to bind or interact with each other specifically. For example, a second affinity molecule is bound to a HRP molecule via complementary oligonucleotides; and a tyramide is bound to a second detection moiety via a binding pair. Accordingly, any number of affinity molecules and corresponding detection moieties can be implemented whereby the complementary molecules or conjugates are specific to each other.

In one embodiment, two different molecules (for example, affinity molecule and oligonucleotide; detection moiety and oligonucleotide; hapten and oligonucleotide; HRP and oligonucleotide; tyramide and oligonucleotide; anti-hapten and oligonucleotide; any additional combinations thereof) can be linked with a cleavable or degradable linker. The cleavable or degradable linker may be used to separate the linked substances in any appropriate manner, including with light (including UV light), chemically, photochemically, enzymatically, or the like.

In one embodiment, multiple rounds of labeling can be performed for cyclic labeling purposes. For example, a target analyte is labeled with a first set of labels, the first set of labels are imaged, the signal provided by the stains are reduced or eliminated (such as with heat (120° C., including at least 30° C., 40° C., 50° C., 60° C., 70° C., 80° C., 90° C., 95° C., 100° C., 105° C., 110° C., 115° C., or 119° C.), light, chemicals, enzymes, molecules having a higher affinity to remove the detection moiety, combinations thereof, and the like in which to reduce or eliminate the signal, such as by denaturing, degrading, cleaving, removing, or modifying), the target analyte is labeled with a second set of labels, and so on until a desired number of biomarkers have been labeled and/or a desired number of rounds have been performed. The heating step can be performed in any device or system appropriate for heating the sample, including, but not limited to, an autostainer, a steamer (such as a vegetable steamer or a bottle sanitizer), a pressure cooker, an autoclave, a water bath, a hot plate, a crockpot, a hair dryer, an incubator, a microwave, or a combination thereof. After addition of the signal disrupter, the sample can be incubated for a sufficient period of time to allow the signal disrupter to modify, reduce, or eliminate the signal. For example, the incubation time can be at least about 30 seconds, at least about 1 minute, at least about 5 minutes, at least about 10 minutes, at least about 15 minutes, at least about 30 minutes, at least about 1 hour, at least about 2 hours, at least about 3 hours, at least about 4 hours, at least about 6 hours, at least about 8 hours, at least about 10 hours, at least about 12 hours, at least about 24 hours, at least about 48 hours or longer.

In one embodiment, complementary oligonucleotides can be de-hybridized by heat (120° C., including at least 30° C., 40° C., 50° C., 60° C., 70° C., 80° C., 90° C., 95° C., 100° C., 105° C., 110° C., 115° C., or 119° C.), light, chemicals, enzymes, molecules having a higher affinity (i.e., strand displacement), combinations thereof, and the like. For example, the complementary oligonucleotides used to form an affinity molecule-horseradish peroxidase conjugate can be de-hybridized when it is desirous or advantageous to do so (for example, when using multiple tyramides for multiple biomarkers and/or for multiple tyramides during multiple rounds of labeling, whether for the same or different biomarkers).

In one embodiment, during the step of reducing or eliminating the signal provided by the stains, at least one molecule complementary to the first and/or second complementary molecule can be added to the sample to inhibit reattachment, reattraction, or re-hybridization of the first and second complementary molecules. For example, the complementary molecule can be an oligonucleotide, an avidin, a biotin, or any other appropriate molecule. The added oligonucleotide can be shorter than, equivalent to, or longer than the first or second complementary molecules.

Labeling

For the sake of convenience, the oligonucleotides of the respective conjugates in FIGS. 1A-3C are denoted as A, A', B, and B', such that A-A' are complementary oligonucleotides and B-B' are complementary oligonucleotides.

FIG. 1A shows one embodiment of a kit for labeling a target analyte with a detection moiety. The kit for making the composition includes an affinity molecule-first oligonucleotide conjugate 102, a horseradish peroxidase ("HRP") molecule-second oligonucleotide conjugate 104, and a tyramide-first detection moiety conjugate 106. The affinity molecule-first oligonucleotide conjugate 102 can be added to the sample first, such that the affinity molecule portion binds or interacts with a desired biomarker. The HRP-second oligonucleotide conjugate 104 can then be added to the sample. The first oligonucleotide of affinity molecule-first oligonucleotide conjugate 102 and the second oligonucleotide of the HRP-second oligonucleotide conjugate 104 are complementary, such that the first and second oligonucleotides hybridize with each other. The HRP molecule and the affinity molecule are, in effect, bound to each via hybridized complementary oligonucleotides. The tyramide-first detection moiety conjugate 106 is then added to the sample. The HRP molecule and the tyramide (of the respective conjugates) undergo a catalytic reaction, whereby the tyramide is activated and deposited at, nearby, or adjacent to the biomarker. The tyramide and the detection moiety of the tyramide-first detection moiety conjugate 106 are directly conjugated.

Figure 1B:
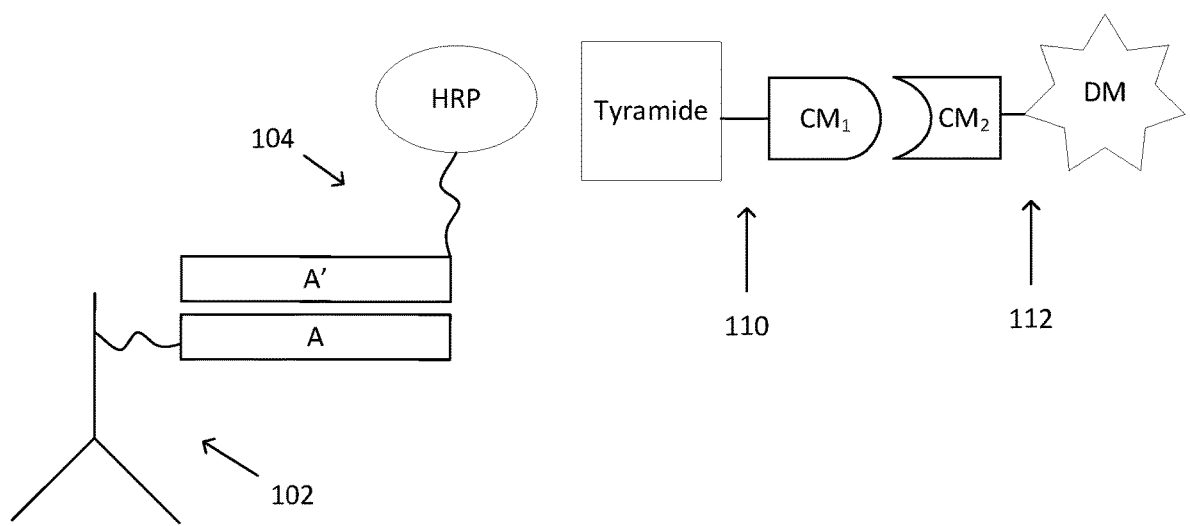

FIG. 1B shows one embodiment of a kit for labeling a target analyte with a detection moiety. The kit for making the composition includes an affinity molecule-first oligonucleotide conjugate 102, a horseradish peroxidase ("HRP") molecule-second oligonucleotide conjugate 104, a tyramide-first complementary molecule conjugate 110, and a detection moiety-second complementary molecule conjugate 112. The affinity molecule-first oligonucleotide conjugate 102 can be added to the sample first, such that the affinity molecule portion binds or interacts with a desired biomarker. The HRP-second oligonucleotide conjugate 104 can then be added to the sample. The first oligonucleotide of affinity molecule-first oligonucleotide conjugate 102 and the second oligonucleotide of the HRP-second oligonucleotide conjugate 104 are complementary, such that the first and second oligonucleotides hybridize with each other. The HRP molecule and the affinity molecule are, in effect, bound to each via hybridized complementary oligonucleotides. The tyramide-first complementary molecule conjugate 110 is then added to the sample. The HRP molecule and the tyramide (of the respective conjugates) undergo a catalytic reaction, whereby the tyramide is activated and deposited at, nearby, or adjacent to the biomarker. The detection moiety-second complementary molecule conjugate 112 can then be added to the sample. The first and second complementary molecules bind or interact with each other. The tyramide and the detection moiety are, in effect, bound to each via the first and second complementary molecules. The first and second complementary molecules (of their respective conjugates) are, in combination, binding pairs, as discussed above. In one embodiment, the first and second complementary molecules are a non-oligonucleotide binding pair. In one embodiment, the first and second complementary molecules are an immune-type binding pair. In one embodiment, the first and second complementary molecules are a non-immune-type binding pair. In one embodiment, the first and second complementary molecules are a hapten-anti-hapten binding pair.

Figure 1C:
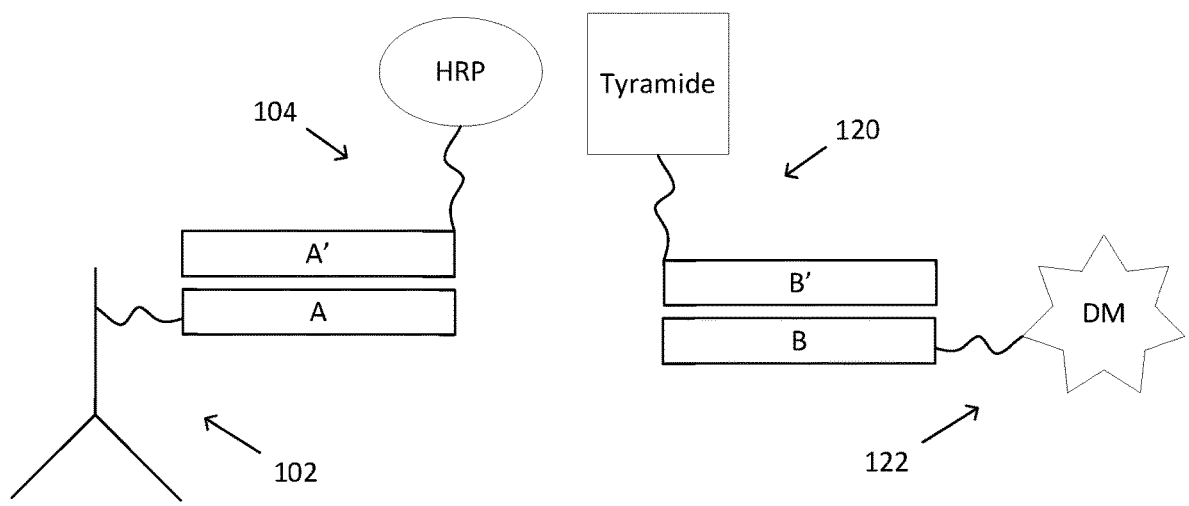

FIG. 1C shows one embodiment of a kit for labeling a target analyte with a detection moiety. The kit for making the composition includes an affinity molecule-first oligonucleotide conjugate 102, a horseradish peroxidase ("HRP") molecule-second oligonucleotide conjugate 104, a tyramide-third oligonucleotide conjugate 120, and a detection moiety-fourth oligonucleotide conjugate 122. The affinity molecule-first oligonucleotide conjugate 102 can be added to the sample first, such that the affinity molecule portion binds or interacts with a desired biomarker. The HRP-second oligonucleotide conjugate 104 can then be added to the sample. The first oligonucleotide of affinity molecule-first oligonucleotide conjugate 102 and the second oligonucleotide of the HRP-second oligonucleotide conjugate 104 are complementary, such that the first and second oligonucleotides hybridize with each other. The HRP molecule and the affinity molecule are, in effect, bound to each via hybridized complementary oligonucleotides. The tyramide-third oligonucleotide conjugate 120 is then added to the sample. The HRP molecule and the tyramide (of the respective conjugates) undergo a catalytic reaction, whereby the tyramide is activated and deposited at, nearby, or adjacent to the biomarker. The detection moiety-fourth oligonucleotide conjugate 122 can then be added to the sample. The first and second complementary molecules bind or interact with each other. The tyramide and the detection moiety are, in effect, bound to each via the third and fourth oligonucleotides.

Though the embodiment above discusses a method and kit in which the conjugates are added in a specific order and/or as distinct components, the method and kit need not be so limiting. For example, in another embodiment, the affinity molecule and the HRP molecule can be bound to each other via the hybridized complementary oligonucleotides prior to adding the conjugates to the sample. The tyramide and the detection moiety can be conjugated (whether directly or indirectly) prior to the adding the conjugates to the sample. In another embodiment, the various conjugates can be added in any order or any combination to label the desired biomarker with the detection moiety.

Figure 2:
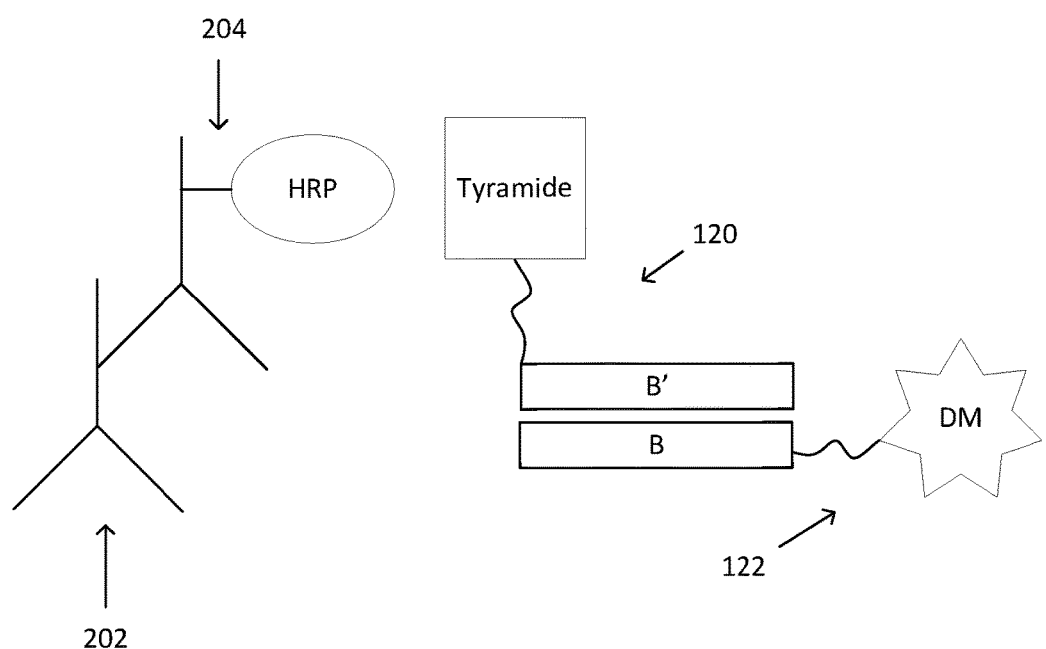
FIG. 2 shows an example detection kit.

FIG. 2 shows another kit for labeling a target analyte with a detection moiety. The kit includes a first affinity molecule 202, an secondary affinity molecule-HRP molecule conjugate 204, the tyramide-first oligonucleotide conjugate 120, and the detection moiety-second oligonucleotide conjugate 122. The first affinity molecule 202 binds to a biomarker on a target analyte. The secondary affinity molecule, such as a secondary antibody, binds to or interacts with the first affinity molecule 202. For example, the first affinity molecule 202 can be a cat, chicken, cow, dog, donkey, goat, guinea pig, hamster, horse, human, llama, monkey, mouse, pig, rabbit, rat, or sheep primary antibody. The secondary affinity molecule of the secondary affinity molecule-HRP molecule conjugate 204 can be an anti-cat, anti-chicken, anti-cow, anti-dog, anti-donkey, anti-goat, anti-guinea pig, anti-hamster, anti-horse, anti-human, anti-llama, anti-monkey, anti-mouse, anti-pig, anti-rabbit, anti-rat, or anti-sheep secondary antibody configured to recognize and bind to or interact with the desired primary antibody (i.e., the first affinity molecule 202).

The tyramide-first oligonucleotide conjugate 120 is then added to the sample. The HRP molecule and the tyramide (of the respective conjugates) undergo a catalytic reaction, whereby the activated and deposited at, nearby, or adjacent to the biomarker. The detection moiety-second oligonucleotide conjugate 122 can then be added to the sample. The first and second oligonucleotides bind or interact with each other. The tyramide and the detection moiety are, in effect, bound to each via the first and second complementary oligonucleotides. In one embodiment, the complementary oligonucleotides can be substituted with other complementary molecules that are complementary oligonucleotides.

Figure 3A:
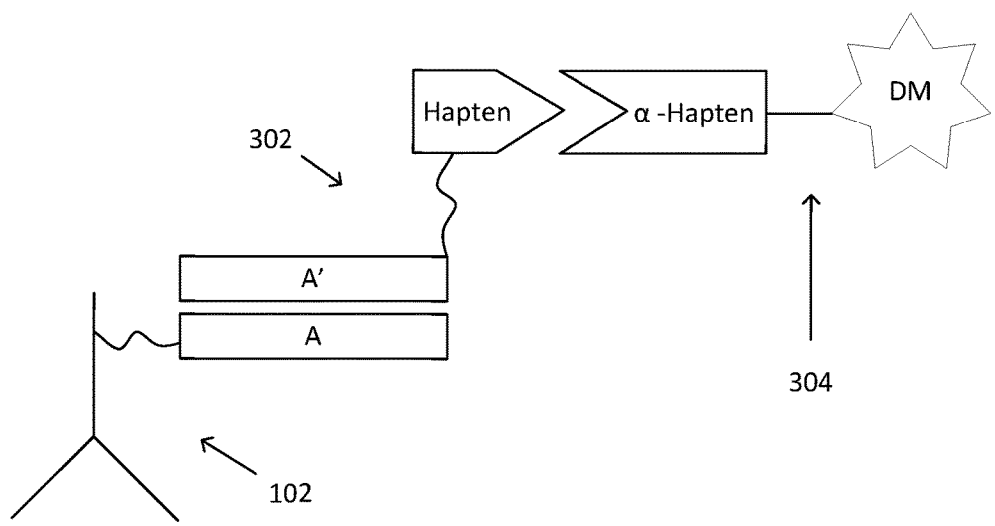
FIGS. 3A, 3B and 3C show example detection kits.

FIG. 3A shows another kit for labeling a target analyte with a detection moiety. The kit for making the composition includes the first affinity molecule-first oligonucleotide conjugate 102, a second oligonucleotide conjugate-first hapten conjugate 302, and a first anti-hapten-first detection moiety conjugate 304. The first affinity molecule binds to a biomarker on a target analyte, the first and second oligonucleotides hybridize, the first hapten binds with the first anti-hapten, and the first detection moiety provides a signal for detecting the biomarker.

Figure 3B:
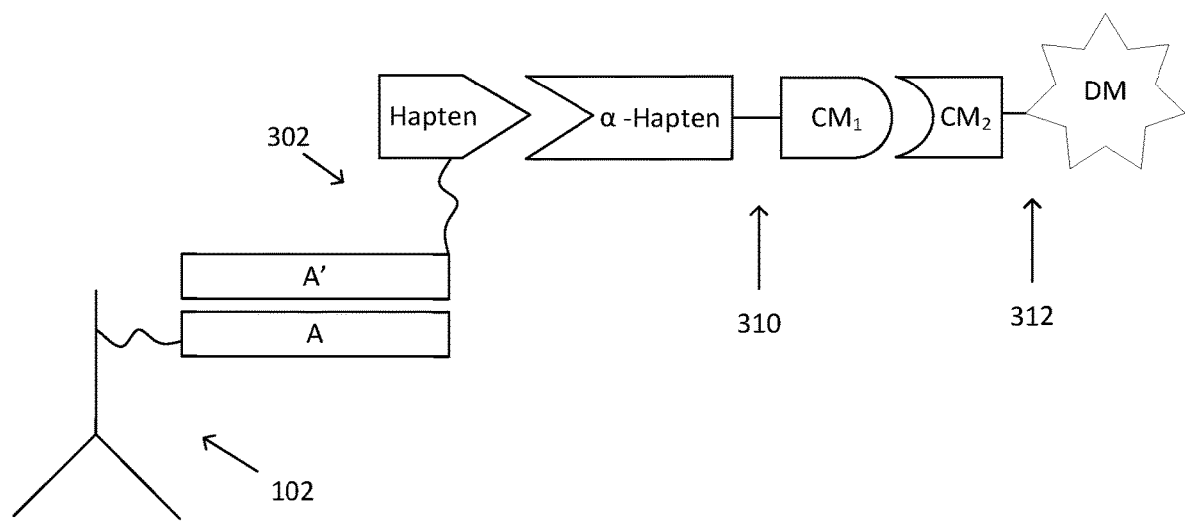

FIG. 3B shows another kit for labeling a target analyte with a detection moiety. The kit for making the composition includes the first affinity molecule-first oligonucleotide conjugate 102, the second oligonucleotide conjugate-first hapten conjugate 302, a first anti-hapten-first complementary molecule conjugate 310, and a second complementary molecule-first detection moiety 312. The first affinity molecule binds to a biomarker on a target analyte, the first and second oligonucleotides hybridize, the first hapten binds with the first anti-hapten, the first and second complementary molecules bind to or interact with each other, and the detection moiety provides a signal for detecting the biomarker. In one embodiment, the first and second complementary molecules are a non-oligonucleotide binding pair. In one embodiment, the first and second complementary molecules are an immune-type binding pair. In one embodiment, the first and second complementary molecules are a non-immune-type binding pair. In one embodiment, the first and second complementary molecules are a hapten-anti-hapten binding pair.

Figure 3C:
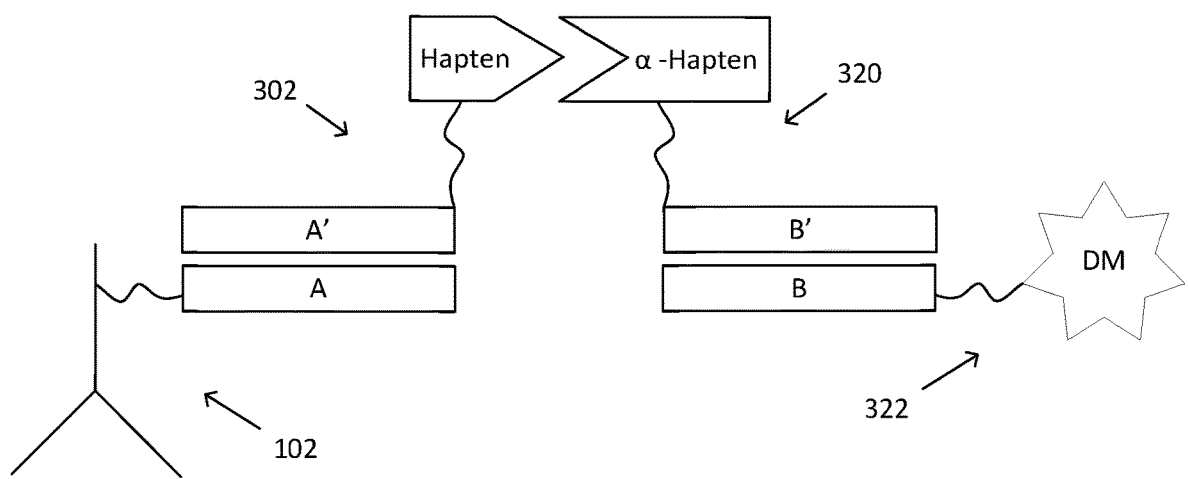

FIG. 3C shows another kit for labeling a target analyte with a detection moiety. The kit for making the composition includes the first affinity molecule-first oligonucleotide conjugate 102, the second oligonucleotide conjugate-first hapten conjugate 302, a first anti-hapten-third oligonucleotide conjugate 320, and a fourth oligonucleotide-first detection moiety 322. The first affinity molecule binds to a biomarker on a target analyte, the first and second oligonucleotides hybridize, the first hapten binds with the first anti-hapten, the third and fourth oligonucleotides hybridize, and the detection moiety provides a signal for detecting the biomarker.

The hapten includes, but is not limited to, a peptide, FITC, DNP, TNP, DIG, and biotin.

The embodiments, as discussed and noted above, can be used to label multiple biomarkers at once or multiple biomarkers in a plurality of rounds. When performing such labeling, the affinity molecules and/or detection moieties can be different between the biomarkers and/or rounds. For example, a first stain (whether used in the same or different round as another stain) can include a first affinity molecule and a first detection moiety, a second stain (whether used in the same or different round as another stain) can include a second affinity molecule and a second detection moiety, and so on, such that the first and second affinity molecule are directed to different biomarkers, and the first and second detection moieties emit different wavelengths.

Biological Example

1. Provide sample.
2. Load onto autostainer (or perform manually, where appropriate).
3. Label at least one biomarker of at least one target analyte with at least one detection moiety.
   a. HRP-Tyramide
      i. Add affinity molecule-first oligonucleotide conjugate
      ii. Add HRP-second oligonucleotide conjugate
      iii. Add tyramide-first complementary molecule conjugate
      iv. Add detection moiety-second complementary molecule conjugate
   b. HRP-Tyramide
      i. Add affinity molecule-first oligonucleotide conjugate
      ii. Add HRP-second oligonucleotide conjugate
      iii. Add tyramide-detection moiety conjugate
   c. Hapten-Anti-Hapten
      i. Add affinity molecule-first oligonucleotide conjugate
      ii. Add hapten-second oligonucleotide conjugate
      iii. Add anti-hapten-detection moiety-second conjugate
   d. Secondary antibody
      i. Add a first antibody-horseradish peroxidase ("HRP") molecule conjugate, wherein the first antibody and HRP are bound via a first secondary antibody
      ii. Add a tyramide-first oligonucleotide conjugate
      iii. Add a second oligonucleotide-first detection moiety conjugate
4. (Optional) Wash with buffer
5. Add coverslip on top of slide
   a. Include mounting medium
   b. Alternatively, use only mounting medium, no coverslip
6. Image the sample.
7. (Optional) Reduce or eliminate the signal generated by the detection moiety
   a. (Optional) Introduce a signal disrupter
8. (Optional) Repeat steps 3-7 at least one more time
9. (Optional) Isolate target analyte
10. (Optional) Process target analyte When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention. Additionally, though "first" and "second" are used, the terms are not intended to limit various features/elements to only one or two. Rather, three (i.e., third), four (i.e., fourth), or more may be included or used where appropriate or desirous to do so.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Though certain examples and embodiments are discussed individually, steps or components can be used together and/or across different embodiments, where it is desirous and/or advantageous to do so. The example and embodiments are intended to be illustrative so as to highlight certain specific aspects or combinations without being so limiting.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated.

What is claimed is:

1. A kit comprising:
a first affinity molecule-first oligonucleotide conjugate;
a horseradish peroxidase ("HRP") molecule-second oligonucleotide conjugate; and
a tyramide-first detection moiety conjugate,
wherein the first and second oligonucleotides are complementary, and
wherein the tyramide and the first detection moiety are conjugated via complementary third and fourth oligonucleotides.

2. The kit of claim 1, further comprising at least one signal disrupter to de-hybridize or cleave the third and fourth oligonucleotides.

3. The kit of claim 1, further comprising at least one signal disrupter to eliminate or reduce a signal capable of being provided by the first detection moiety.

4. The kit of claim 1, further comprising:
a second affinity molecule-third oligonucleotide conjugate;
a horseradish peroxidase ("HRP") molecule-fourth oligonucleotide conjugate;
a tyramide-second detection moiety conjugate,
wherein the third oligonucleotide of the second affinity molecule-third oligonucleotide conjugate and the fourth oligonucleotide of the HRP molecule-fourth oligonucleotide conjugate are complementary.

5. The kit of claim 4, wherein the first and second affinity molecules are directed to different biomarkers.

6. The kit of claim 4, wherein the first and second detection moieties have different emission wavelengths.

7. The kit of claim 4, further comprising at least one signal disrupter to de-hybridize or cleave at least one of the first and second oligonucleotides or the third oligonucleotide of the second affinity molecule-third oligonucleotide conjugate and the fourth oligonucleotide of the HRP molecule-fourth oligonucleotide conjugate.

8. The kit of claim 4, further comprising at least one signal disrupter to eliminate or reduce a signal capable of being provided by at least one of the first and second detection moieties.

9. A kit comprising:
a first affinity molecule-first oligonucleotide conjugate;
a horseradish peroxidase ("HRP") molecule-second oligonucleotide conjugate;
a tyramide-first detection moiety conjugate,
a second affinity molecule-third oligonucleotide conjugate;
a HRP molecule-fourth oligonucleotide conjugate; and
a tyramide-second detection moiety conjugate,
wherein the first and second oligonucleotides are complementary,
wherein the third and fourth oligonucleotides are complementary,
wherein the tyramide and the first detection moiety of the tyramide-first detection moiety conjugate are conjugated via complementary fifth and sixth oligonucleotides; and wherein the tyramide and the second detection moiety of the tyramide-second detection moiety conjugate are conjugated via complementary seventh and eighth oligonucleotides.

10. The kit of claim 9, further comprising at least one signal disrupter to de-hybridize or cleave one or more of the oligonucleotide pairs.

11. A method for labeling a target analyte of a sample, the method comprising:
adding, to the sample, a first affinity molecule-first oligonucleotide conjugate;
adding, to the sample, a horseradish peroxidase ("HRP") molecule-second oligonucleotide conjugate; and
adding, to the sample, a tyramide-first detection moiety conjugate,
wherein the first and second oligonucleotides are complementary and hybridize with each other, and
wherein the tyramide and the first detection moiety are conjugated via complementary third and fourth oligonucleotides.

12. The method of claim 11, wherein the tyramide-first detection moiety conjugate is added after the first affinity molecule-first oligonucleotide conjugate and the HRP-second oligonucleotide.

13. The method of claim 11, wherein the tyramide-first detection moiety conjugate is conjugated before the step of adding the tyramide-first detection moiety conjugate.

14. The method of claim 11, wherein the step of adding the tyramide-first detection moiety conjugate further comprises the steps of:
adding, to the sample, a tyramide-third oligonucleotide conjugate; and
adding, to the sample, a fourth oligonucleotide-first detection moiety conjugate.

15. The method of claim 11, further comprising the steps of:
observing a first signal of the first detection moiety; and
modifying the first signal with a signal disrupter,
wherein the observing the first signal and modifying the first signal steps are performed after the adding steps.

16. The method of claim 15, wherein the signal disrupter de-hybridizes the third and fourth oligonucleotides.

17. The method of claim 11, further comprising:
adding, to the sample, a second affinity molecule-third oligonucleotide conjugate;
adding, to the sample, a horseradish peroxidase ("HRP") molecule-fourth oligonucleotide conjugate; and
adding, to the sample, a tyramide-second detection moiety conjugate,
wherein the third and fourth oligonucleotides are complementary.

18. The method of claim 17, wherein the first and second affinity molecules are directed to different biomarkers.

19. The method of claim 17, wherein the first and second detection moieties have different emission wavelengths.

20. The method of claim 17, further comprising the steps of:
observing a first signal of the first detection moiety; and
modifying the first signal with a signal disrupter.

21. The method of claim 20, further comprising the step of observing a second signal of the second detection moiety, wherein the first and second signals have the same emission wavelength, and wherein the observing and modifying steps for the first signal of the first detection moiety are performed before adding the tyramide-second detection moiety conjugate.

22. A method for labeling a target analyte of a sample, the method comprising:
adding, to the sample, a first affinity molecule-first oligonucleotide conjugate;
adding, to the sample, a horseradish peroxidase ("HRP") molecule-second oligonucleotide conjugate;
adding, to the sample, a tyramide-first detection moiety conjugate,
adding, to the sample, a second affinity molecule-third oligonucleotide conjugate;
adding, to the sample, a HRP molecule-fourth oligonucleotide conjugate; and
adding, to the sample, a tyramide-second detection moiety conjugate,
wherein the first and second oligonucleotides are complementary,
wherein the third and fourth oligonucleotides are complementary,
wherein the tyramide and the first detection moiety of the tyramide-first detection moiety conjugate are conjugated via complementary fifth and sixth oligonucleotides; and
wherein the tyramide and the second detection moiety of the tyramide-second detection moiety conjugate are conjugated via complementary seventh and eighth oligonucleotides.

* * * * *